United States Patent [19] … [11] 4,329,506
Velenyi et al. … [45] May 11, 1982

[54] ISOMERIZATION OF ALDEHYDES TO KETONES

[75] Inventors: Louis J. Velenyi, Lyndhurst; Andrew S. Krupa, Twinsburg, both of Ohio

[73] Assignee: The Standard Oil Company, Cleveland, Ohio

[21] Appl. No.: 182,282

[22] Filed: Aug. 28, 1980

[51] Int. Cl.$^3$ .............................................. C07C 45/51
[52] U.S. Cl. .................................. 568/310; 568/384; 568/341
[58] Field of Search ............... 568/310, 341, 384, 312, 568/388, 389

[56] References Cited

U.S. PATENT DOCUMENTS 3,384,668 5/1968 Canter et al. ....................... 568/388
3,453,331 7/1969 Hargis et al. ....................... 568/388
3,966,822 6/1976 Fukui et al. ....................... 568/388
4,200,589 4/1980 Scharf ................................. 568/389

OTHER PUBLICATIONS

Ishimura, Bulletin Chem. Soc., Japan, vol. 16, pp. 191–209 and 252–262 (1941).

Primary Examiner—Natalie Trousof
Assistant Examiner—James H. Reamer
Attorney, Agent, or Firm—Gary R. Plotecher; Herbert D. Knudsen; Larry W. Evans

[57] ABSTRACT

Aldehydes, such as isobutyraldehyde, are isomerized to ketones, such as methyl ethyl ketone, by contact at isomerization conditions, typically vapor-phase conditions, with a catalyst of the formula $M_{0.15-15} M'_{0.05-12} O_x$ where M is at least one of Mo and Cu and M' is a promoter, such as a Group IIB or VIII element.

7 Claims, No Drawings

ISOMERIZATION OF ALDEHYDES TO KETONES

BACKGROUND OF THE INVENTION

1. Field of the Invention

This invention relates to the isomerization of aldehydes to ketones.

2. Description of the Prior Art

Canter, et al., U.S. Pat. No. 3,384,668, teach the isomerization of aliphatic aldehydes to ketones by contacting a vaporous aldehyde with a solid acidic catalyst, e.g. phosphoric acid on a support, at a temperature above 100° C.

Hargis et al., U.S. Pat. No. 3,453,331, teach the production of symmetrical and unsymmetrical ketones from aldehydes by contacting an aldehyde with an oxidized form of a rare earth metal having an atomic number of 59 to 71 supported on an activated alumina. The process is a vapor-phase process.

Other processes are known. See for example the references cited at column 1, lines 23–27, of Canter et al.

SUMMARY OF THE INVENTION

According to this invention, aldehydes are isomerized to ketones by a process comprising contacting at isomerization conditions an aldehyde with a catalyst of the formula $$M_{0.15-15}M'_{0.05-12}O_x \qquad (I)$$

where

M is at least one of Mo and Cu,

M' is at least one of tin, lead, chromium, tungsten, gold, silver, selenium, antimony, bismuth, vanadium, phosphorus, arsenic, cerium, tellurium, thorium, uranium and a Group IA, IIA, IIB, IVB or VIII element, and x is the number of oxygen atoms determined by the valence requirements of the other elements present, with the proviso that the mole quotient of M/M' is greater than or equal to 1.

The process is typically conducted in the vapor phase and is applicable to a wide variety of aldehydes.

DETAILED DESCRIPTION OF THE INVENTION

Any aldehyde that can be isomerized to a ketone can be used in the practice of this invention. Typical aldehydes are of the formula $$\begin{array}{c} R\ \ O \\ |\ \ \| \\ R'-C-C-H \\ | \\ R'' \end{array} \qquad (II)$$

where R, R' and R'' are hydrogen, aliphatic, alicyclic, aryl or an inertly-substituted aliphatic, alicyclic or aryl radical with the proviso that all are not simultaneously hydrogen, aryl or inertly-substituted aryl. Preferably R, R' and R'' are independently hydrogen, $C_1$–$C_4$ alkyl or phenyl. Preferably the aldehyde contains but a single aromatic group, i.e. only one of R, R' and R'' is phenyl. "Inertly-substituted" and like terms here mean that the R, R' and R'' substituents can bear functional groups, e.g. alkoxys, halogen, etc., that are essentially nonreactive with the starting materials, catalysts and products of the process at process conditions. Representative aldehydes include propanal, n-butanal, pentanal, isobutyraldehyde, 2-phenyl-propanal, 2,2-diphenyl-propanal, etc. Isobutyraldehyde and 2-phenyl-propanal are preferred aldehydes.

The ketones produced by this invention are the isomerized products of a starting aldehyde. Aldehydes of formula (II) produce ketones of the formula $$\begin{array}{c} H\ \ O \\ |\ \ \| \\ R'-C-C-R \\ | \\ R'' \end{array} \qquad (III)$$

where R, R' and R'' are as defined in formula (II).

The catalysts here used are compounds of formula I where M, M' and x are as previously defined. Preferably, M is a combination of Mo and Cu, M' is at least one of Sn, V and W, the subscript of M is a number of at least 1 and the subscript of M' is a number of about 0.5 to about 8. The promoter elements, M', can be present in their zero oxidation state or in a higher oxidation state, and generally the mole quotient of M/M' is greater than 3.

The catalysts can be used in either their 100% active form or diluted with other materials, e.g. loaded onto a carrier. If diluted, generally any carrier can be used with silica, alumina, silica-alumina, titania, zeolite, zirconia, silicon carbide, carbon, magnesia, compatible organic and inorganic polymers, etc. all being exemplary. Carriers of alumina, silica and silica-alumina are preferred. If a support is used, the catalytic composition is generally present in an amount of at least about 10 weight percent, based on the combined weight of the support and catalytic composition, and preferably in an amount of at least about 30 weight percent.

The catalytic compositions of this invention can be prepared by any one of a number of different methods, the particular method employed being a matter of convenience. These methods include both aqueous and nonaqueous, e.g. alcoholic, methods of preparation. In a typical aqueous preparation, the catalysts are prepared by mixing the appropriate catalyst ingredients in the proper proportions in an aqueous mixture, drying the resulting aqueous slurry with or without a reducing agent, and calcining the product. The ingredients can be added in any order during the preparation procedure but preferably the metallic ingredients are mixed prior to the addition of any nonmetallic ingredients. Ingredients employed can be the oxides, halides, nitrates, acetates or other salts of the particular metals or elements added and particularly preferred is the use of water soluble salts of the metal components. If a support is used, the material comprising the support may be incorporated into the catalyst along the other ingredients or the catalytic composition can be coated and/or impregnated onto or into the support. After the catalyst ingredients have been combined to form an aqueous slurry, the slurry is taken to dryness and the dried solid obtained is heated in the presence of air, nitrogen, nitric oxide, etc. at a temperature between about 300° and 420° C. This calcination can take place outside the catalytic reactor or an in situ activation can be utilized. Other methods of preparation are broadly taught in the art.

As taught by formula I, M can be a combination of Mo and Cu and M' can be a combination of two or more promoter elements. Where M or M' is such a combination, the subscript value represents the sum of the elements (e.g. where M' is a combination of tungsten and vanadium, the sum of the tungsten and vanadium present is a number of about 0.05 to about 12). The individual subscript values of the components, e.g. the individual subscript values for vanadium and tungsten, can vary to convenience.

The exact structure or elemental arrangement of these catalysts is not known but the components are present in the form of their oxides or oxide complexes. However, the compositions of formula I are known not to be a mere physical mixture of their components but rather unique entities where the individual components are chemically and/or physically bonded to one another.

Isomerization conditions are used in the practice of this invention and these will vary with the aldehydes, catalysts, reactor, etc. employed. This process is a heterogeneous catalytic process, i.e. the catalyst is in the solid state while the aldehyde is either in the gaseous or liquid state. Preferably, the aldehyde is in the gaseous state when contacted with the catalyst.

Any temperature at which the aldehyde is either a liquid or gas can be employed with a typical minimum temperature being about 200° C. and preferably about 250° C. Economy, convenience and degradation of aldehyde, ketone and catalyst are the principal constraints upon the maximum temperature employed and a typical maximum temperature is about 550° C. and is preferably about 450° C. Pressure is important primarily as it relates to temperature and pressures ranging from subatmospheric to superatmospheric can be used.

If the aldehyde is in the gaseous state at the reaction temperature, then it can be used by either itself or diluted with a relatively inert sweep gas, such as nitrogen, argon, helium, carbon dioxide, steam and the like. Likewise, if the aldehyde is a liquid at the reaction temperature, then it also can be used either alone or with a suitable diluent. Representative diluents include mixed hexanes and heptanes, cyclohexane, benzene, etc.

Contact or residence time can also vary widely, depending upon such variables as the aldehyde, catalyst, reactor, temperature and pressure. Typical contact times range from a fraction of a second to more than several hours with preferred contact times, at least for gaseous phase reactions, between about 0.5 and 10 seconds.

Typically the catalyst is employed in a fixed- or ebullient-bed reactor where the reactant, typically in the gaseous form, is passed over or through the catalyst. Other reactors can be used.

The following examples are illustrative embodiments of this invention. Per pass conversion (PPC) is calculated by dividing the moles of total product times 100 by the moles of aldehyde fed. The selectivity was calculated by dividing the PPC to the ketone by the PPC of the total product.

SPECIFIC EMBODIMENTS

Catalyst Preparation

A catalyst consisting, in weight percent, of $$30\% (Mo_5Cu_4SnO_x) \; 52.5\% \; SiO_2 \; 17.5\% \; Al_2O_3 \quad (IV)$$

was prepared by dissolving 6.36 g of copper acetate in 800 cc of distilled water to yield a clear blue solution. To this solution was added 14.39 g ammonium heptamolybdate. The mixture was brought to boiling but a complete solution was not attained. A light-green precipitate was present. To this mixture was added 3.01 g of stannic oxide powder and the entire mixture was brought to a boil for ½ hours after which 101.4 g of 41% colloidal silicon dioxide and 13.86 g of Dispal M alumina were added. The resulting mixture was then evaporated to a thick, light-green paste, dried for 4 hours at about 110° C. and the resulting hard, light-green material was calcined for 2 hours at 380° C. in a muffle furnace. The final product was a very hard, light-green material which was ground to 10–30 mesh (U.S. Standard).

Procedure

The catalyst was charged to a 20 cc down-flow, fixed-bed reactor. The aldehyde was then fed to the reactor, together with steam and nitrogen, at a given temperature and the product collected and analyzed. The off-gas was passed through a cold acetone scrubber where the liquid products were retained. These liquid products were then quantitatively analyzed using a Hewlett-Packard gas chromatograph.

EXAMPLE 1

Using the catalyst and procedure described above, 2-phenyl propionaldehyde was converted to phenyl acetone (benzylmethyl ketone) at 350° C. and atmospheric pressure with a 3.3 second contact time. The aldehyde was quantitatively converted with a selectivity to the phenyl acetone of 66.8%.

EXAMPLE 2

Again using the catalyst and the procedure described above, isobutyraldehyde was converted to methyl ethyl ketone at about 450° C. and atmospheric pressure with a contact time of about 5 seconds. About 37% conversion of the aldehyde was obtained with about 19% selectivity to the ketone.

EXAMPLE 3

Using the procedure described above but with air in the feed gas and with a catalyst of the formula $$20\% (Mo_{12}Cu_2Sn_{0.5}V_3W^o{}_{1.2}O_x) \; 80\% \; SA \; 203 \quad (V)$$

2-phenyl propionaldehyde was converted to cyclic ketone, 2-indanone, at 250° C. and atmospheric pressure with a contact time of about 3 seconds. SA 203 is an α-alumina manufactured by Norton Company. The per pass conversion of the aldehyde was about 28% with a selectivity to the cyclic ketone of about 58%.

Although the invention has been described in detail by the preceeding examples, this detail is for the purpose of illustration only and is not intended as a limitaton upon the spirit and scope of the appended claims.

What is claimed is:

1. A process of isomerizing aldehydes to ketones, the process comprising contacting at isomerization conditions an aldehyde with a catalyst of the formula $$M_{0.15-15} \; M'_{0.05-12} \; O_x \quad (I)$$

where
M is a combination of Mo and Cu,
M' is tin, and
x is the number of oxygen atoms determined by the valence requirements of the other elements present, with the proviso that the mole quotient of M/M' is greater than or equal to 1.

2. The process of claim 1 where the subscript value of M is a number of at least one and the subscript value of M' is a number of about 0.5 to about 8.

3. The process of claim 2 where the mole quotient of M/M' is greater than 3.

4. The process of claim 3 where the aldehyde is of the formula

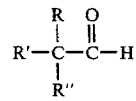

where R, R' and R" are hydrogen, aliphatic, alicyclic or aryl or an inertly-substituted aliphatic, alicyclic or aryl radical with the proviso that all are not simultaneously hydrogen, aryl or inertly-substituted aryl.

5. The process of claim 4 where R, R' and R" are independently hydrogen, $C_1$–$C_4$ alkyl or phenyl.

6. The process of claim 5 where the compound of formula II is isobutyraldehyde or 2-phenyl-propanal.

7. The process of claim 6 where the contacting is conducted at atmospheric pressure and at a temperature between about 200° C. and about 550° C.

* * * * *